US00PP32514P2

(12) United States Plant Patent
Wood

(10) Patent No.: US PP32,514 P2
(45) Date of Patent: Nov. 24, 2020

(54) ***HYDRANGEA* PLANT NAMED 'SMNHMP'**

(50) Latin Name: *Hydrangea macrophylla*
Varietal Denomination: SMNHMP

(71) Applicant: Spring Meadow Nursery, Inc., Grand Haven, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/602,615

(22) Filed: Nov. 7, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHMP' is disclosed, characterized by floriferous plants with strong stems producing extra-large inflorescences. Plants rebloom and are hardy in USDA Zones 5 through 9. Plants respond to commercial bluing treatment, inflorescences can be bright pink or purple-violet, depending upon culture. The new variety is a *Hydrangea*, normally produced as an ornamental plant.

3 Drawing Sheets

Latin name of the genus and species: *Hydrangea macrophylla.*

Variety denomination: 'SMNHMP'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties that are more floriferous, with new colors, and stronger stems. The cross resulting in this new variety was made during 2011.

The seed parent is the unpatented variety *Hydrangea macrophylla* 'Cityline Lisbon'. The pollen parent is the unpatented variety *Hydrangea macrophylla* 'Wyatt LeFever'. The new variety was identified as a potentially interesting selection in 2014, at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHMP' by vegetative softwood cuttings was first performed during 2014, at a commercial greenhouse in Grand Haven, Mich. Subsequent asexual propagation has shown that the unique features of this cultivar are stable and reproduced true to type in 5 successive generations.

SUMMARY OF THE INVENTION

The cultivar 'SMNHMP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHMP' These characteristics in combination distinguish 'SMNHMP' as a new and distinct *Hydrangea* cultivar:

1. Very floriferous.
2. Strong stems.
3. Extra-large inflorescences, which can be bright pink or purple-violet.
4. Reblooming.
5. Hardy in USDA Zones 5-9.

PARENT COMPARISON

Plants of the new cultivar 'SMNHMP' are similar to plants of the seed parent in most horticultural characteristics, however, plants of the new cultivar 'SMNHMP' differ in the following;

1. The new variety has a darker, more intense flower color than the seed parent.

Plants of the new cultivar 'SMNHMP' are similar to plants of the pollen parent in most horticultural characteristics, however, plants of the new cultivar 'SMNHMP' differ in the following;

1. The new variety has a darker, more intense flower color than the pollen parent.
2. The new variety has larger leaves than the pollen parent.
3. The new variety has darker green foliage than the pollen parent.

COMMERCIAL COMPARISON

Plants of the new cultivar 'SMNHMP' can be compared to the variety *Hydrangea macrophylla* 'SMNHMSIGMA', U.S. Plant Pat. No. 26,929. These varieties are similar in most horticultural characteristics; however 'SMNHMP' differs in the following:

1. The new variety has a tighter flower head than this comparator.
2. Acidic flowers of the new variety are more purple; acidic flowers of this comparator are more blue.

BRIEF DESCRIPTION OF THE PHOTOGRAPHS

'SMNHMP' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

FIG. 1 shows plants of 'SMNHMP' grown in a greenhouse in Grand Haven, Mich. in 2019. The plant on the left of the photo has been treated with a typical acidic "bluing" (aluminum sulfate) treatment. The plant to the right has not been given the bluing treatment. Plant form is illustrated as well.

DETAILED BOTANICAL DESCRIPTION

Figure 1:
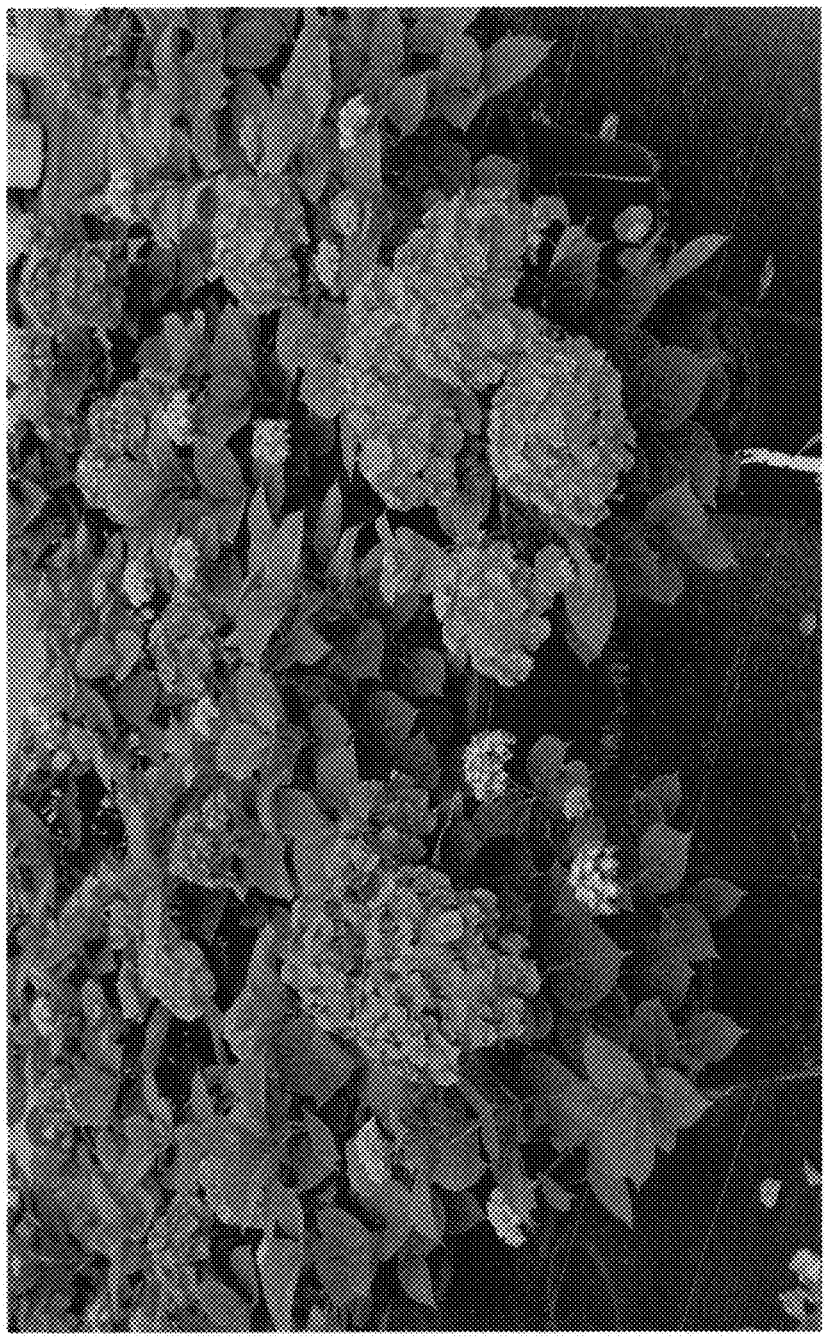
Figure 2:
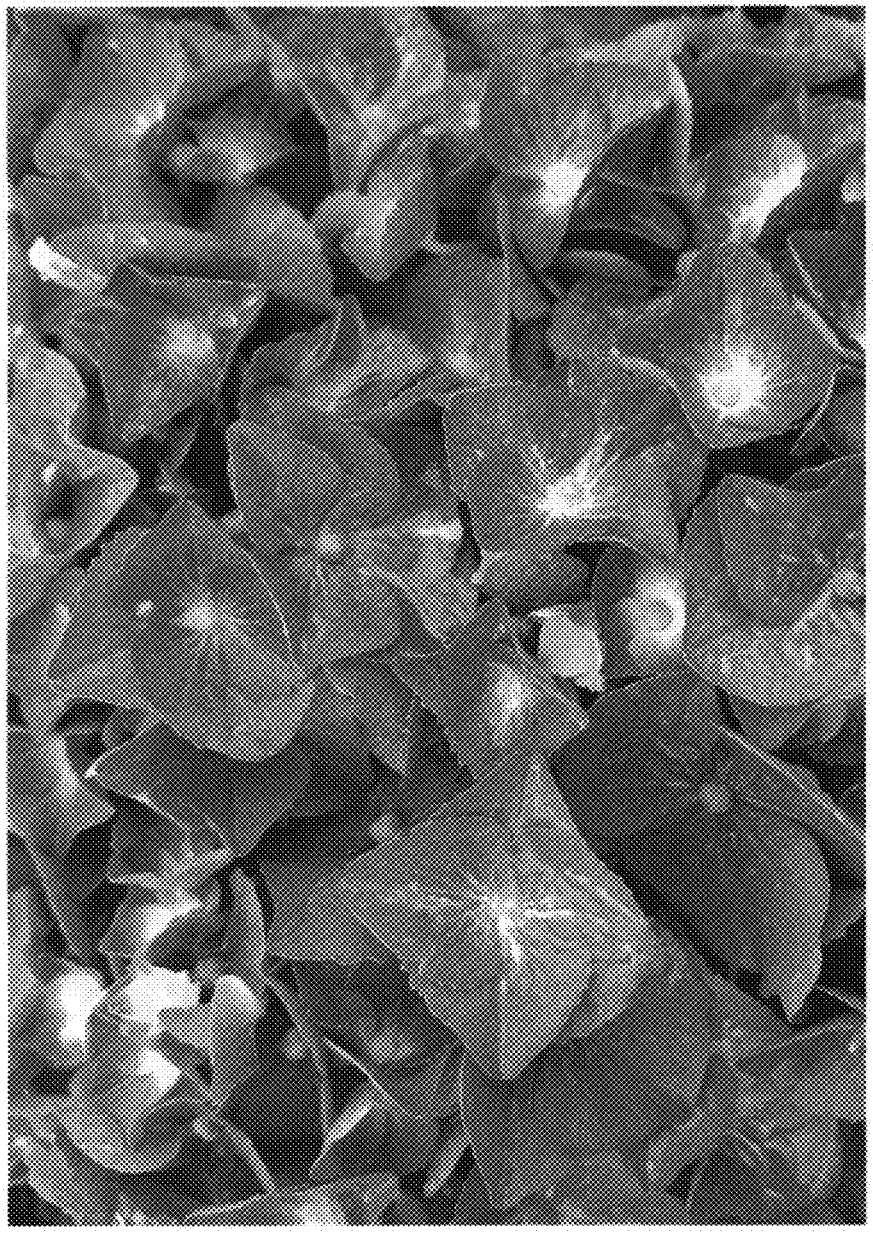
FIG. 2 shows the mature flower color of a container-grown plant, treated with "bluing" treatment, grown in a greenhouse in Grand Haven, Mich. in 2019.
Figure 3:
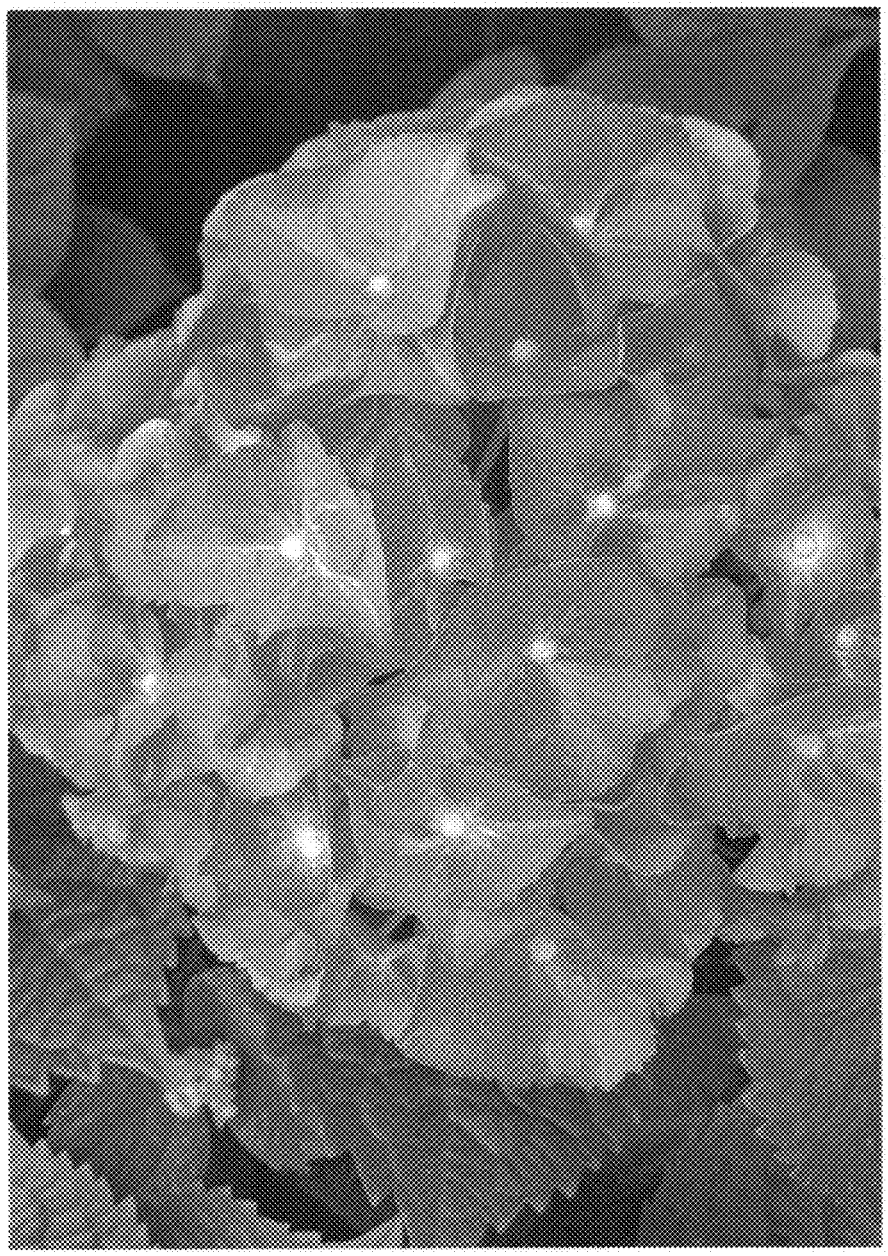
FIG. 3 shows the mature flower color of a container-grown plant, treated without "bluing" treatment, grown in a greenhouse in Grand Haven, Mich. in 2019.

In the following description, color references are made to The Royal Horticultural Society Color Chart 2015 except where general terms of ordinary dictionary significance are used. The following observations and measurements describe 'SMNHMP' plants grown in a commercial poly greenhouse in Grand Haven, Mich. under natural lighting. Measurements were taken during Summer of 2019. The plants were about 4 years old planted in the ground. The growing temperature ranged from 5° C. to 27° C. Measurements and numerical values represent averages of typical plant types.

Botanical classification: *Hydrangea macrophylla* 'SMNHMP'.

PROPAGATION

Time to initiate roots: Approximately 18 days.
Time to produce a rooted young plants: Approximately 60 days.
Propagation method: Softwood cuttings.

PLANT

Plant type: Flowering deciduous perennial shrub.
Age of plant described: Approximately 2 to 3 years old.
Growth habit: Upward and a little outward.
Overall plant shape: Rounded.
Height: 41 cm.
Plant spread: 66 cm.
Growth rate: Good.
Plant vigor: Good.
Branching habit: Basal, some pinching required.
Length of primary lateral branches: 38 cm.
Diameter of lateral branches: 6 mm.
Quantity of lateral branches: 15 to 20.
Stem:
- *Stem shape*.—Round.
- *Stem strength*.—Strong.
- *Color*.—Immature: RHS Green 143B. Mature: RHS Green 143B.
- *Pubescence*.—None.
- *Aspect*.—15 to 45°.

Internode length: 5 cm.
Lenticels:
- *Color*.—RHS Greyed-Orange 165A.

Root description: Moderately dense, thick main roots with fine, fibrous secondary roots. Main roots colored near Brown 200D, secondary roots near Yellow-White 158D.

FOLIAGE

Leaf:
- *Arrangement*.—Opposite.
- *Leaf shape*.—Ovate.
- *Average length*.—9.5 cm.
- *Average width*.—6.5 cm.
- *Apex*.—Cuspidate.
- *Base*.—Cuneate.
- *Margin*.—Serrate.
- *Texture of top surface*.—Leathery.
- *Texture of bottom surface*.—Leathery, ribbed.
- *Leaf pubescence*.—None.
- *Color*.—Young foliage upper side: Near RHS Green 137A. Young foliage under side: RHS Green 138B. Mature foliage upper side: RHS Green 139A. Mature foliage under side: RHS Green 139C.
- *Venation*.—Pattern: Pinnate. Color upper side: RHS Green 139C. Color under side: RHS Yellow-Green 143D.
- *Petiole*.—Average Length: 1.2 cm. Diameter: 5 mm. Petiole color upper side: RHS Green 139C. Petiole color lower side: RHS Green 143D. Petiole Texture upper side: Smooth, slightly pubescent. Petiole Texture lower side: Slightly pubescent.

FLOWER

Natural flowering season: Summer.
Inflorescence:
- *Type*.—Mophead.
- *Quantity of flowers per inflorescence*.—Fertile flowers: About 25. Sterile flowers: 50 to 150.
- *Persistent or self-cleaning*.—Self-cleaning, after several weeks.
- *Longevity*.—Individual flowers stay fresh on the plant for about 2 weeks. Inflorescences are ornamental for several weeks.
- *Fragrance*.—None detected.

Panicle:
- *Shape*.—Dome.
- *Height*.—8 cm.
- *Diameter*.—17 cm.

Sterile flower:
- *Bud shape*.—Obovate.
- *Bud length*.—3 mm.
- *Bud diameter*.—3 mm.
- *Bud color*.—RHS Yellow-Green 145D.
- *Flower aspect*.—Upright and outward.
- *Flower shape*.—Round.

*Flower length.*—3.5 cm.
*Flower diameter.*—3.5 cm.
*Persistence.*—Self-cleaning.

Sterile flower petals:
*Petal arrangement.*—Whorl.
*Quantity.*—4.
*Length of petal.*—4 mm.
*Width of petal.*—3 mm.
*Apex.*—Acute.
*Shape of petal.*—Ovate.
*Petal margin.*—Entire.
*Petal base.*—Truncate.
*Petal texture.*—Smooth, upper and under side.
*Color.*—Upper surface at first opening: Acidic: RHS Blue 106B. Basic: RHS Purple 75C. Under surface at first opening: Acidic: RHS Blue 106B. Basic: RHS Purple 75C. Upper surface at maturity: Acidic: RHS Blue 106B. Basic: RHS Purple 75C. Under surface at maturity: Acidic: RHS Blue 106B. Basic: RHS Purple 75C.

Sterile flower sepal:
*Arrangement.*—Whorl.
*Number.*—4.
*Shape.*—Obovate.
*Tip.*—Obtuse.
*Base.*—Cuneate.
*Margin.*—Entire.
*Length.*—2 cm.
*Width.*—2 cm.
*Texture, upper.*—Smooth.
*Texture, lower.*—Smooth.
*Color.*—Upper surface at first opening: RHS Yellow-Green 149C. Under surface at first opening: RHS Yellow-Green 149C. Upper surface at maturity: Acidic: RHS Purple-Violet N80B. Basic: RHS Red-Purple 67B. Under surface at maturity: Acidic: RHS Purple-Violet N80C. Basic: RHS Red-Purple 67B, lightly streaked 67D.

Sterile flower pedicel:
*Length.*—1.5 cm.
*Diameter.*—2 mm.
*Angle.*—45°.
*Strength.*—Good.
*Texture.*—Smooth, pubescent.
*Color.*—Acidic: RHS Violet-Blue 96C. Basic: RHS Red-Purple 73A.

Fertile flower:
*Bud shape.*—Obovate.
*Bud length.*—4 mm.
*Bud diameter.*—34 mm.
*Bud color.*—Acid treatment: Near RHS Violet-Blue 98C. Basic treatment: near RHS Red-Purple 73C.
*Texture.*—Glabrous.

Flower:
*Shape.*—Star-shaped.
*Length.*—1.3 cm.
*Depth.*—4 mm.
*Diameter.*—1.3 cm.
*Flower aspect.*—Upright, outward.
*Persistence.*—Self-cleaning.
*Longevity.*—1 to 2 weeks.

Fertile flower petals:
*Arrangement.*—Whorl.
*Quantity.*—5.
*Length of petal.*—5 mm.
*Width of petal.*—2 mm.
*Apex.*—Acute.
*Shape of petal.*—Ovate.
*Petal margin.*—Entire.
*Petal base.*—Cuneate.
*Petal texture.*—Smooth, upper and under side.
*Color.*—Upper surface at first opening: RHS Yellow-Green 145B. Under surface at first opening: RHS Yellow-Green 145B. Upper surface at maturity: Acidic: RHS Violet-Blue 91B. Basic: RHS Red-Purple 63C. Under surface at maturity: Acidic: RHS Violet-Blue 91B. Basic: RHS Red-Purple 63C.

Fertile flower sepal: None.

Fertile flower pedicel:
*Angle.*—45°.
*Strength.*—Good.
*Length.*—5 mm.
*Width.*—1 mm.
*Texture.*—Smooth.
*Color.*—Acidic: RHS Violet-Blue 96C. Basic: RHS Red-Purple 73A.

REPRODUCTIVE ORGANS

Sterile flowers:
Stamens:
*Number.*—7.
*Filament length.*—1 mm.
*Filament color.*—RHS Red-Purple 73D.
Anthers:
*Shape.*—Round.
*Length.*—5 mm.
*Color.*—RHS White 155B.
*Pollen.*—Amount: Scant to moderate. Color: RHS White 155B.
Pistil:
*Number.*—2.
*Length.*—0.5 mm.
*Stigma.*—Shape: Lobed. Color: RHS Red-Purple 73D.
*Style.*—Length: 0.5 mm. Color: RHS Red-Purple 73D.

Fertile flowers:
Stamens:
*Number.*—10.
*Filament length.*—2 mm.
*Filament color.*—RHS White 155B.
Anthers:
*Shape.*—Round.
*Length.*—1 mm.
*Color.*—RHS White 155B.
*Pollen color.*—RHS White 155B.
*Pollen amount.*—Scant to moderate.
Pistil:
*Number.*—3.
*Length.*—1 mm.
*Style.*—Length: 0.5 mm. Color: RHS White NN155B. Ovary color: RHS White NN155B.
*Stigma.*—Shape: Lobed. Color: RHS White NN155B.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 4 to 9.

What is claimed is:

1. A new and distinct cultivar of *Hydrangea* plant named 'SMNHMP' as herein illustrated and described.

* * * * *